Figure 1:
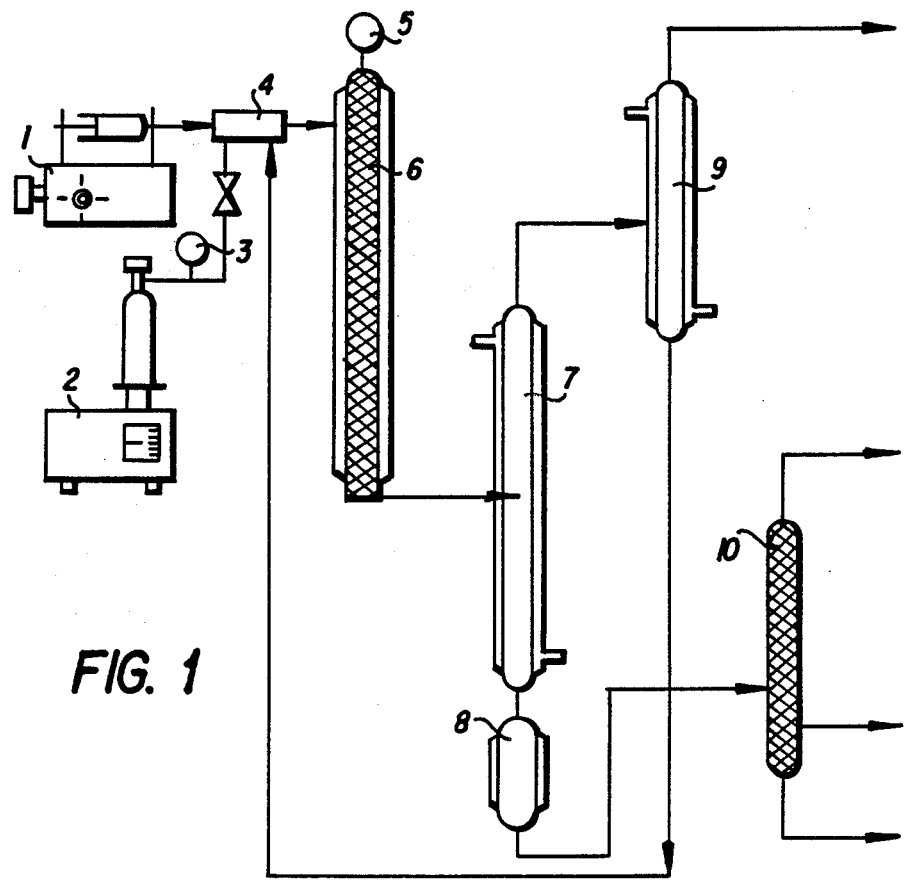

United States Patent [19]

Grego et al.

[11] Patent Number: 4,916,256

[45] Date of Patent: Apr. 10, 1990

[54] PROCESS FOR THE PRODUCTION OF ALKYL TRIFLUOROACETATES

[75] Inventors: Saverio Grego, Venezia-Mestre; Adriano Checchin, Venice; Giorgio Guglielmo, Mirano-Venezia, all of Italy

[73] Assignee: Ausimont, S.p.A., Milan, Italy

[21] Appl. No.: 233,854

[22] Filed: Aug. 18, 1988

Related U.S. Application Data

[63] Continuation of Ser. No. 886,928, Jul. 18, 1986, abandoned.

[30] Foreign Application Priority Data

Jul. 19, 1985 [IT] Italy ................................ 21652 A/85

[51] Int. Cl.$^4$ .............................................. C07C 67/14
[52] U.S. Cl. ................................................... 560/227
[58] Field of Search ......................................... 560/227

[56] References Cited

PUBLICATIONS

Yasnitskii, et al., Chem. Abst., 59:7371g (1963).

Primary Examiner—Michael L. Shippen
Attorney, Agent, or Firm—Stevens, Davis, Miller & Mosher

[57] ABSTRACT

Process for the production of alkyl trifluoroacetates by esterification of trifluoroacetyl chloride with alkyl alcohols, wherein the trifluoroacetyl chloride/alcohol molecular ratio is greater than 1; alkyl trifluoroacetate is recovered by condensation at temperatures lower than −30° C.

8 Claims, 1 Drawing Sheet

U.S. Patent    Apr. 10, 1990    4,916,256

PROCESS FOR THE PRODUCTION OF ALKYL TRIFLUOROACETATES

This application is a continuation of application Ser. No. 886,928, filed July 18, 1986, now abandoned.

The present invention relates to a process for the production of alkyl trifluoroacetates.

More particularly, the present invention relates to a process for the production of trifluoroacetate of an alkyl group containing a low number of carbon atoms, by starting from trifluoroacetyl chloride.

The preparation of esters of trifluoroacetic acid starting from trifluoroacetyl chloride is known from technical literature. In particular, G.D. R. Pat. No. 29,513 to L. Heinrich discloses the preparation of trifluoroacetic acid alkyl esters. The process disclosed in this patent comprises flowing a mixture of $CF_3COF$ or $CF_3COCl$, $SO_2$ and $Br_2$, in the gaseous state, through alcohol at a purity of 99%, and at temperatures comprised within the range of from $-20°$ C. to alcohol boiling temperature; preferably at room temperature.

The esterification is carried out in the absence of acid-acceptor agents, and the ester produced is separated by pouring the alcoholic solution into a water-ice mixture, containing a water-insoluble solvent of the ester having a specific gravity higher than 1 $kg/dm^3$, and having a boiling point higher by at least $30°$ C. than ester boiling point.

The ester produced is submitted to some purification treatments, e.g., washing with water, neutralization with an aqueous solution of $NaHCO_3$, drying over $CaCl_2$, before being sent to the distillation to separate it from the other reaction products.

This process suffers from considerable technological drawbacks, which make it not much attractive from the viewpoint of its application on full industrial scale.

It has been now surprisingly found by the Applicant, and is the object of the present invention, that the technological drawbacks above mentioned can be eliminated by carrying out the reaction between trifluoroacetyl chloride and an alkyl alcohol of general formula R—OH, wherein R is an alkyl group containing from 1 to 4 carbon atoms, with a trifluoroacetyl chloride/alkyl alcohol molecular ratio greater than 1, and recovering the ester formed by condensation at temperatures lower than $-30°$ C.

According to a preferred embodiment, the reaction can be carried out with a trifluoroacetyl chloride/alkyl alcohol molecular ratio comprised within a range of from 1.1 to 2, and preferably of from 1.2 to 1.4.

In the process of the present invention, any temperature can be used, although temperatures of from $50°$ C. to $130°$ C. are preferred. In particular, if R is an ethyl group, the temperature is comprised within the range of from $90°$ C. to $100°$ C., and if R is a methyl group, the temperature is comprised within the range of from $75°$ C. to $85°$ C. The time of reaction between the reactants is generally very short, and can range from 3 to 60 seconds, preferably from 5 to 10 seconds.

The reaction can be carried out indifferently as a continuous, batch, or semi-continuous process.

In case of a batch process, trifluoroacetyl chloride is fed in gas phase into the alcohol in the liquid state, charged inside a reactor kept at reaction temperature. To the contrary, in case of a continuous process, trifluoroacetyl chloride and the alcohol are fed together, in the vapour phase, to a tubular reactor.

The process of the present invention allows the alkyl trifluoroacetate to be obtained at a purity higher than 90%, and of up to 99%, increasing such purity to an end value very close to 100% by rectification being possible.

The reaction products leaving the reactor are fed to a partial condensation column kept at temperatures lower than $-30°$ C., wherein the alkyl ester of trifluoroacetic acid condenses.

Said alkyl ester is collected in a vessel and is heated to a temperature of from $30°$ C. to $100°$ C., to the purpose of removing possible residues of hydrogen chloride formed during the reaction, and of unreacted trifluoroacetyl chloride.

If the ester produced is the ethyl ester, such a temperature is preferably comprised within the range of from $55°$ to $60°$ C., if the ester is methyl ester, such a temperature is preferably comprised within the range of from $35°$ C. to $40°$ C.

The stream of hydrogen chloride formed, and the excess of trifluoroacetyl chloride are sent to a second partial condensation step, at temperatures lower than $-50°$ C., wherein only trifluoroacetyl chloride condenses and is recycled to the esterification reactor.

According to an alternative route, unreacted trifluoroacetyl chloride can be recovered also by chemical way, by esterification with a molar excess of the same alkyl alcohol, to obtain the highest possible conversion of trifluoroacetyl chloride.

In such an esterification, the alkyl alcohol/unreacted trifluoroacetyl chloride molecular ratio is comprised within the range of from 1.1 to 1.5, and preferably of from 1.15 to 1.3.

The ester produced in such a reaction, containing unreacted alcohol, is condensed and recycled to the esterification reactor.

Whether the first or the second recovery method is used, the ester produced has a purity of from 97 to 99%, and can be further purified by rectification, to reach a purity very close to 100%.

Figure 2:
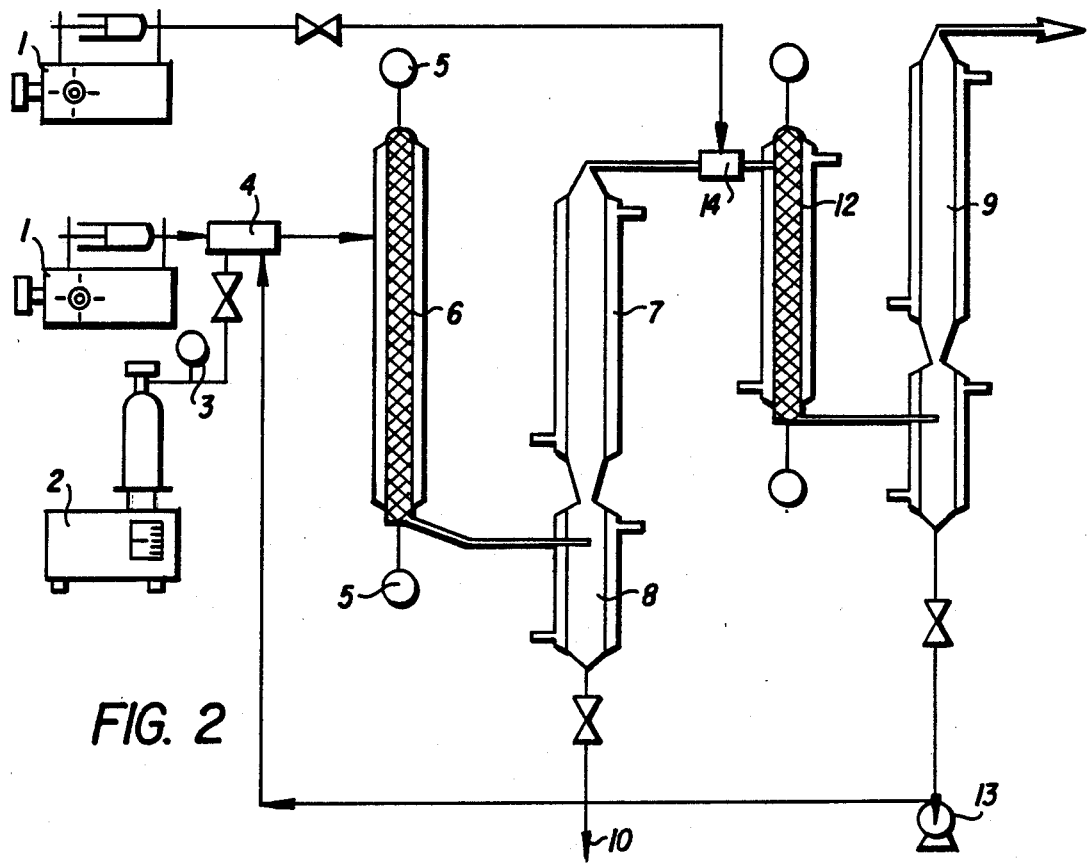

For a more detailed description of the process of the present invention, reference is made to the diagrams of FIGS. 1 and 2.

Referring to FIG. 1, to the mixer (4) the alcohol, by the metering pump (1), and trifluoroacetyl chloride containing in tank (2) are fed; the pressure of gas outflowing from (2) is controlled by the pressure regulator (3).

The reactants are fed in vapour phase to reactor (6), the temperature of which is checked by the temperature indicator (5).

The reaction products are discharged from reactor bottom, and are sent to the partial condenser (7) for the recovery of the alkyl ester.

Condensed ester is collected inside tank (8), and from there it is sent to the rectification column (10) from which, by a side drawing, the product is recovered at a purity level higher than 99.8%; low-boiling and high-boiling side products are discharged as the overhead and the bottom fraction respectively.

From the head of partial condenser (7), hydrogen chloride produced during the esterification reaction, and the excess of trifluoroacetyl chloride are sent to a second partial condenser (9), wherein the condensation occurs of trifluoroacetyl chloride only; this latter is recycled to reactor (6), after a preliminary vapourization in (4), whilst hydrogen chloride, still in the gas phase, is discharged to undergo further treatments.

Should it be desired to recover the excess of trifluoroacetyl chloride by chemical way rather than by physical way, the products from the esterification reaction are treated by operating according to the diagram shown in FIG. 2.

The products outflowing from the top of partial condenser (7), and constituted by hydrogen chloride and trifluoroacetyl chloride are reacted, after a preliminary vapourization in (14), with the same alcohol, fed by a second metering pump (11), inside a secondary esterification reactor (12); in this case, the alcohol/trifluoroacetyl chloride ratio is greater than 1, so to have an as high as possible conversion of trifluoroacetyl chloride.

The reaction products and unreacted materials are sent to the partial condenser (9), on the bottom of which a mixture of ester, alcohol and possibly traces of unreacted trifluoroacetyl chloride are collected and recycled by the pump (13) to the esterification reactor (6).

To the purpose of better understanding the present invention, and of showing practical embodiments thereof, some illustrative, non-limitative Examples are reported hereunder.

EXAMPLE 1

Preparation of the ethyl ester by one reactor only

To a pyrex-glass tube, reactor (6), with diameter=14 mm and length=640 mm, provided with a jacket to allow it to be heated, packed with glass spheres (diameter=3-4 mm), with a free volume of 50 cc, over a 1-hour time, 0.592 mol of trifluoroacetyl chloride (as gas) and 0.4872 mol of ethanol are fed, their mutual molecular ratio being 1.21. The reactor is kept at the controlled temperature of 100° C., and the contact time is of 5-6 seconds. The gas outflowing from reactor (6), having the following composition by volume:

| | |
|---|---|
| Ester | 45.1% |
| Hydrogen chloride | 45.1% |
| Trifluoroacetyl chloride | 9.5% |
| Low-boiling and high-boiling products | 0.3% | is fed to a partial condensation column (7), kept at −30° C. The condensate is heated to 60° C. in the apposite collecting vessel (8), to completely remove trifluoroacetyl chloride and hydrogen chloride from the ester. From the gas stream leaving (7), and constituted by 0.4870 mol of hydrochloric acid and 0.105 mol of trifluoroacetyl chloride, trifluoroacetyl chloride is recovered by condensation in (9) at −60° C.; trifluoroacetyl chloride in the liquid phase is recycled, after a preliminary vapourization, to reactor (6).

The raw ester (69.8 g), collected in (8), is already at a high purity level (about 99); converted trifluoroacetyl chloride=82.4%; yield to ester relatively to converted trifluoroacetyl chloride=99%.

If an ester with higher purity is desired, the ester obtained is rectified up to a purity higher than 99.8%.

EXAMPLE 2

Preparation of the methyl ester by one reactor only

To the reactor of Example 1, over a 1-hour time, 0.6795 mol of trifluoroacetyl chloride and 0.50235 mol of methanol are fed (molecular ratio=1.3). The reactor is kept at 80° C., and the contact time is of 6 seconds. The gas outflowing from reactor (6), having the following composition by volume:

| | |
|---|---|
| Ester | 43.8% |
| Hydrogen chloride | 43.8% |
| Trifluoroacetyl chloride | 12.2% |
| Other products | 0.2% | is fed to a partial condensation column (7), kept at −30° C.; the condensate is heated to 40° C. in the apposite collecting vessel (8), to completely remove trifluoroacetyl chloride and hydrogen chloride from the ester.

From the overhead gas stream leaving (7), constituted by 0.50 mol of hydrochloric acid and 0.17 mol of trifluoroacetyl chloride, cooled in (9) to −60° C., the excess of trifluoroacetyl chloride is recovered via condensation and is recycled to (6).

The raw ester condensed in (8) (65 g), has already a purity of about 99%; converted trifluoroacetyl chloride=74%; yield to ester relatively to converted trifluoroacetyl chloride=about 99%.

If an ester at a higher purity level is desired, the above product is rectified up to a purity higher than 99.8%.

EXAMPLE 3

Preparation of the ethyl ester by two reactors

To the reactor (6) of FIG. 2, over a 1-hour time, 0.6338 mol of trifluoroacetyl chloride and 0.4889 mol of ethanol are fed, their mutual molecular ratio being 1.3.

The temperature of reactor (6) is kept at 85° C., and the contact time is of 6 seconds.

The gas outflowing from reactor (6) is treated as described in Example 1. The condensate in (8), 66 g, has the following composition by weight:

| | |
|---|---|
| Ester | 99.00% |
| Low-boiling products | 0.75% |
| Diethyl carbonate | 0.25% |

By rectification, ethyl trifluoroacetate at 99.8% is obtained.

The gas stream leaving (7), having the following molar composition: trifluoroacetyl chloride=21.86%; HCl=73.76%; ester=4.37%, is fed, together with ethanol (0.2276 mol, ethanol/trifluoroacetyl chloride molecular ratio=1.57), to a second reactor, similar to the first one, but of 14 mm in diameter, 380 mm in length and having a free volume of 30 cc, kept at 80° C. by a liquid means circulating inside its jacket, and with a contact time of five seconds.

The product stream leaving the second reactor (12) is sent to the condenser (9), kept at −70° C., to condense the ester, and unreacted ethanol and trifluoroacetyl chloride, which are collected and recycled to reactor 6.

Hydrogen chloride outflows from the head of condensation column, and is sent to the neutralization.

The condensate—which is recycled—(32 g), has the following composition by weight:

| | |
|---|---|
| Ester | 64.40% |
| Trifluoroacetyl chloride | 8.11% |
| Hydrogen chloride | 4.63% |
| Ethanol | 12.78% |
| Low-boiling products | 1.08% |

Converted trifluoroacetyl chloride=97%; yield to ester relatively to converted trifluoroacetyl chloride=99%.

EXAMPLE 4

Preparation of the ethyl ester by two reactors

To the reactor (6) of FIG. 2, over a 1-hour time, 0.512 mol of trifluoroacetyl chloride and 0.273 mol of ethanol are fed, together with a recycle (outcoming from a previous run) constituted by 0.108 mol of ethanol, 0.0517 mol of ester and 0.0652 mol of hydrogen chloride. The trifluoroacetyl chloride/ethanol molecular ratio is 1.34. The temperature of reactor (6) is kept controlled at 85° C., and the contact time is of 5 seconds.

The outflow from (6) is treated as in preceding Example 3.

The raw ester condensed in (7), 61 g, has the following composition by weight:

| | |
|---|---|
| Ester | 98.84% |
| Low-boiling products | 0.83% |
| Diethyl carbonate | 0.33% |

By rectification, an ester with a purity level higher than 99.8% is obtained.

The gas stream leaving (7), having the following molar percent composition: hydrogen chloride=76.23%; trifluoroacetyl chloride=22.4%; ester=1.36%, is fed, together with ethanol (0.1572 mol; ethanol/trifluoroacetyl chloride molecular ratio=1.2) to the second reactor (12), kept at 85° C., with a contact time of 5 seconds.

The outflow leaving (12) is partly condensed in (9) (see preceding Example 3), and is recycled to (6). It has the following composition by weight:

| | |
|---|---|
| Ester | 61.84% |
| Ethanol | 11.52% |
| Trifluoroacetyl chloride | 6.64% |
| Hydrogen chloride | 16.00% |

The hydrogen chloride overhead stream from column (9) is sent to the neutralization.

Converted trifluoroacetyl chloride=98%; yield to ester relatively to converted trifluoroacetyl chloride=97%.

EXAMPLE 5

Preparation of the methyl ester by two reactors

To the reactor (6) of FIG. 2, over a 1-hour time, 0.7035 mol of trifluoroacetyl chloride and 0.5522 mol of methanol are fed. Their mutual molecular ratio is 1.27.

The temperature of reactor (6) is kept at 77° C., and the contact time is of 5 seconds.

The gas stream leaving reactor (6) is treated as described in Example 3. The raw ester, 63.6 g, kept in (8) at 25° C., has a purity of 99%. By rectification, an ester having a purity higher than 99.8% is obtained.

The gas stream leaving the condensation column (7), having the following molar percent composition:

| | |
|---|---|
| Trifluoroacetyl chloride | 19.63% |
| HCl | 72.27% |
| Ester | 7.85% | is fed, together with ethanol (0.1886 mol, methanol/trifluoroacetyl chloride molecular ratio=1.24), to a second reactor (12), kept at the temperature of 75° C., and with a contact time of 5 seconds.

The product stream leaving the second reactor (12) is condensed in (9), as in Example 3, and recycled to (6); the amount thereof is 36.5 g, and it has the following composition by weight:

| | |
|---|---|
| Ester | 56.1% |
| Methanol | 7.53% |
| Trifluoroacetyl chloride | 17.64% |
| Hydrogen chloride | 18.74% |

Hydrogen chloride leaves condenser (9) as the overhead fraction, and is sent to the neutralization.

In the overall, converted trifluoroacetyl chloride is 93%, and the yield to ester relatively to converted trifluoroacetyl chloride is of 99%.

We claim:

1. Process for the production of alkyl trifluoroacetate by esterification of trifluoroacetyl chloride with an alkyl alcohol of the formula R-OH, with R being an alkyl group having from 1 to 4 carbon atoms, with a trifluoroacetyl chloride/alkyl alcohol molecular ratio between 1.1 and 2.

2. Process according to claim 1, wherein the alkyl alcohol is methanol.

3. Process according to claim 1, wherein the alkyl alcohol is ethanol.

4. Process according to claim 1, wherein the esterification reactor is carried out at a temperature comprised within the range of from 50° C. to 100° C.

5. Process according to claim 2, wherein the esterification reaction is carried out at a temperature comprised within the range of from 75° C. to 85° C.

6. Process according to claim 3, wherein the esterification reaction is carried out at a temperature comprised within the range of from 90° C. to 100° C.

7. Process according to claim 1, wherein the alkyl ester produced is recovered by partial condensation of the gaseous reaction mixture at a temperature lower than −30° C.

8. Process according to claim 1, wherein the trifluoroacetyl chloride/alcohol ratio is within the range of from 1.2 to 1.4.

* * * * *